United States Patent [19]
Antons et al.

[11] Patent Number: 5,859,298
[45] Date of Patent: Jan. 12, 1999

[54] PROCESS FOR THE PREPARATION OF 2-HALOGENO-4,5-DIFLUOROBENZOYL FLUORIDES

[75] Inventors: Stefan Antons; Albrecht Marhold, both of Leverkusen; Bernhard Beitzke, Rösrath, all of Germany

[73] Assignee: Bayer Aktiengesellschaft, Leverkusen, Germany

[21] Appl. No.: 799,902

[22] Filed: Feb. 13, 1997

Related U.S. Application Data

[63] Continuation of Ser. No. 403,313, Mar. 14, 1995, abandoned.

[30] Foreign Application Priority Data

Mar. 21, 1994 [DE] Germany .......................... 44 09 578.3

[51] Int. Cl.[6] ..................................................... C07L 51/58
[52] U.S. Cl. ............................................................. 562/864
[58] Field of Search ...................................... 562/864, 564

[56] References Cited

U.S. PATENT DOCUMENTS

| | | |
|---|---|---|
| 4,851,160 | 7/1989 | Peterson et al. . |
| 4,990,661 | 2/1991 | Petersen et al. . |
| 5,072,038 | 12/1991 | Klauke et al. . |

FOREIGN PATENT DOCUMENTS

| | | |
|---|---|---|
| 0164619 | 12/1985 | European Pat. Off. . |
| 0266512 | 5/1988 | European Pat. Off. . |
| 3420796 | 12/1985 | Germany . |

*Primary Examiner*—Paul J. Killos
*Attorney, Agent, or Firm*—Sprung Kramer Schaefer & Briscoe

[57] ABSTRACT

2-Halogeno-4,5-difluoro-benzoyl fluorides are obtained in high yields by reacting 2,4-dichloro-5-fluoro-benzoyl halides with potassium fluoride in an aprotic solvent. The 2-halogeno-4,5-difluoro-benzoyl fluorides prepared in this way are particularly suitable as intermediates for the preparation of antibacterial active substances.

6 Claims, No Drawings

PROCESS FOR THE PREPARATION OF 2-HALOGENO-4,5-DIFLUOROBENZOYL FLUORIDES

This application is a continuation of application Ser. No. 08/403,313, filed on Mar. 14, 1995 which is abandoned.

The present invention relates to a particularly advantageous process for the preparation of 2-(fluoro or chloro)-4,5-difluoro-benzoyl fluoride from 2,4-dichloro-5-fluorobenzoyl chloride or fluorid 2-Chloro-4,5-difluoro-benzoyl chloride, the corresponding benzoic acid and the corresponding benzyl alcohol are valuable intermediates for the preparation of 7-(substituted)piperazinyl-1-(substituted)-6-fluoro-1,4-dihydro-4-oxo-2-quinoline-carboxylic acids, which are antibacterial active substances (see e.g. U.S. Pat. No. 4,833,270). In these compounds it is apparently the fluorine atoms in position 4 and 5 which are of particular importance, since they are present unchanged in the antibacterial active substance whereas the fluorine atom in position 2 is eliminated along the route to the antibacterial active substance, and thus this position in the intermediate may be occupied by a chlorine atom (see also EP-A 303 291).

Starting from 2-(fluoro or chloro)-4,5-difluoro-benzoyl fluoride, the corresponding benzoyl chloride, the corresponding benzoic acid and the corresponding benzyl alcohol are accessible in a conventional manner.

It is known that 2,4,5-trifluoro-benzoyl fluoride can be prepared from 2,4-dichloro-5-fluoro-benzoyl fluoride by the action of potassium fluoride in the presence of an aprotic solvent (see DE-A 34 20 796). The yield in this reaction is 65.5% of theory (see Example 1 of the DE-A). Whether and, if so, to which products the remaining 34.5% of the starting material is reacted are matters which are not disclosed. There therefore remains a need for a process for the preparation of intermediates for antibacterial active substances, in which these intermediates are obtained in higher yields.

A process has now been found for the preparation of 2-halogeno-4,5-difluoro-benzoyl fluorides of the formula (I)

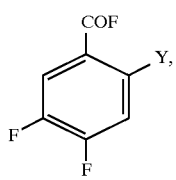

in which
Y represents fluorine or chlorine,
which is characterized in that a 2,4-dichloro-5-fluorobenzoyl halide of the formula (II)

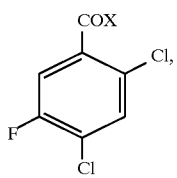

in which
X represents fluorine or chlorine
is reacted with potassium fluoride in an aprotic solvent.

The starting compound of the formula (II) where X=chlorine, which can be employed in the process according to the invention, can be obtained in a known manner from 3-fluorotoluene. The second starting compound (formula (II) with X=fluorine) which can be employed in the process according to the invention can be prepared therefrom by conventional fluorination using anhydrous hydrogen fluoride. In the process according to the invention it is preferred to employ 2,4-dichloro-5-fluorobenzoyl fluoride (formula (II) where X=fluorine) since in this case less potassium fluoride is required.

At least 1 mol of potassium fluoride is generally employed in the process according to the invention per equivalent of chlorine atoms to be substituted; this corresponds to at least 1 mol of potassium fluoride per mole of starting compound of the formula (II) where X=fluorine and at least 2 mol of potassium fluoride per mole of starting compound of the formula (II) where X=chlorine.

It is preferred to employ from 1.05 to 2.0 mol, particularly preferably from 1.1 to 1.5 mol, of potassium fluoride per equivalent of chlorine atoms to be substituted. Larger quantities of potassium fluoride, for example more than 2.5 mol per equivalent of chlorine atoms to be substituted, have virtually no effect on the degree of fluorination and are therefore disadvantageous on economic grounds.

Examples of suitable aprotic solvents for the process according to the invention are dimethylformamide, dimethyl sulphoxide, N-methylpyrrolidone, dimethyl sulphone and tetramethylene sulphone (=sulpholane). It is preferred to employ tetramethylene sulphone. The solvent can be employed, for example, in quantities of from 200 to 1000 ml per mole of starting material of the formula (II).

The process according to the invention can be carried out, for example, at temperatures in the range from 150° to 270° C. Temperatures in the range from 180° to 230° C. are preferred.

The reaction time may be, for example, between 1 and 12 hours. When 2,4-dichloro-5-fluoro-benzoyl fluoride is used it is preferred to carry out the reaction according to the invention only until all of the starting material has been consumed.

For the process according to the invention the pressure is not especially critical, and can be selected almost as desired. In general, therefore, the process is carried out at from 0.5 to 5 bar and, in particular, at atmospheric pressure.

The reaction mixture can be worked up, for example, by a procedure in which it is distilled, preferably at reduced pressure. This leads to 2-halogeno-4,5-difluorobenzoyl fluorides of the formula (I) in good yields and purities, and often to mixtures of 2-fluoro- and 2-chloro-4,5-difluorobenzoyl fluorides, which are suitable for being processed further to give medicaments.

In a preferred embodiment of the process according to the invention the procedure is to place potassium fluoride in tetramethylene sulphone and to distil off a small quantity of tetramethylene sulphone under reduced pressure in order to remove any small quantities of water which may be present. The mixture is then cooled somewhat, 2,4-dichloro-5-fluorobenzoyl fluoride is added, and the mixture is heated with stirring at the desired reaction temperature until all of the starting material has reacted. The mixture is then cooled again somewhat and the 2,4,5-trifluoro- and 2-chloro-4,5-difluorobenzoyl fluoride obtained are distilled off at a pressure in the range from 50 to 200 mbar.

The process according to the invention has the surprising advantage that it can be used to obtain intermediates for the preparation of antibacterial active substances (mostly mixtures of 2,4,5-trifluoro- and 2-chloro-4,5-difluoro-benzoyl fluoride) in yields of more than 75% of theory, often more than 85% of theory. A further surprise is that the isomer 4-chloro-2,5-difluorobenzoyl fluoride, which cannot be used for the preparation of antibacterial active substances, is formed in the process according to the invention either not at all or only in traces of far less than 1%.

Starting from the 2-halogeno-4,5-difluoro-benzoyl fluorides of the formula (I) which are accessible in accordance with the invention, it is possible in a conventional and simple manner to obtain the corresponding benzoyl chlorides, benzoic acids and benzyl alcohols, whose use for the preparation of antibacterial active substances is known from the literature. For example, it is possible for compounds of the formula (I)

a) to be reacted first with acid and then with thionyl chloride to give the corresponding benzoyl chlorides, or b) to be reacted with silicon tetrachloride, optionally in the presence of catalytic quantities of aluminium trichloride, or with calcium chloride, likewise to give the corresponding benzoyl chlorides, or c) to be reduced with sodium borohydrides to give the corresponding benzyl alcohols, or d) first to be reacted in accordance with a) or b) to give benzoyl chlorides which can be converted by hydrolysis into the corresponding benzoic acid.

EXAMPLES

Example 1

A mixture of 203.5 g of potassium fluoride and 500 ml of sulpholane was heated at 200° C. in a 4-necked flask with stirrer, thermometer, nitrogen inlet and distillation bridge. 50 ml of sulpholane were distilled off at an overhead temperature of 170° to 180° C. by applying a vacuum. The mixture was cooled to 150° C. and then 211 g of 2,4-dichloro-5-fluorobenzoyl chloride were added and the mixture was stirred at 200° C. for 2 hours until all of the 2,4-dichloro-5-fluorobenzoyl chloride had reacted. The reaction mixture was subsequently distilled at 100 mbar to give 171 g of distillate. The distillate consisted of 50.5% by weight of 2,4,5-trifluorobenzoyl fluoride and 49.0% by weight of 2-chloro-4,5-difluorobenzoyl fluoride and contained only traces 4-chloro-2,5-difluorobenzoyl fluoride. The distillate therefore contained more than 99% by weight of the desired products.

Example 2

50 ml of sulpholane were distilled off (in vacuo) from a mixture of 500 ml of sulpholane and 232.4 g of potassium fluoride, and then 227.5 g of 2,4-dichloro-5-fluorobenzoyl chloride were added at 150° C. After reaction for 2 hours at 200° C. and distillation of the mixture, 179 g of product were obtained. This product contained 52.7% by weight of trifluorobenzoyl fluoride, 46.7% by weight of 2-chloro-4,5-difluoro-benzoyl fluoride, 0.3% by weight of 2,4-dichloro-5-fluoro-benzoyl fluoride and 0.2% by weight of 4-chloro-2,5-difluorobenzoyl fluoride. The distillate therefore contained 99.4% by weight of the desired products.

Examples 3 to 7

The procedure of Example 1 was followed but changing the quantities of potassium fluoride employed and the reaction time. The results obtained are compiled in Table 1 below.

| Ex. No. | Moles of KF per mole of 2,4-dichloro-5-fluoro-benzoyl fluoride | Reaction time (h) | Yields in % of theory | | | Desired products |
|---|---|---|---|---|---|---|
| | | | 2,4,5-tri-fluoro- | 2-chloro-4,5-difluoro-benzoyl fluoride | 4-chloro-2,5-difluoro- | |
| 3 | 4 | 4 | 60.5 | 15.8 | 0.2 | 76.3 |
| 4 | 3.5 | 4 | 60.6 | 30.6 | 0.05 | 91.2 |
| 5 | 3.5 | 2.5 | 40.2 | 49.8 | 0.1 | 90.0 |
| 6 | 3.2 | 4 | 37.0 | 41.5 | 0.1 | 78.5 |
| 7 | 3.1 | 5 | 63.2 | 22.6 | 0.05 | 85.8 |

Example 3 shows that continuing the fluorination leads in practice to losses in the yield of desired products. This effect is markedly reduced when the quantity of potassium fluoride is decreased (see Examples 4 and 5). Example 6 likewise shows that good results are achieved even with a little potassium fluoride. From Example 7 it is evident that good results can still be achieved with only a small excess of potassium fluoride if the reaction time is made correspondingly longer.

What is claimed is:

1. A process for producing a mixture containing 2,4,5-trifluoro benzoyl fluoride and 2-chloro-4,5-difluoro-benzoyl fluoride and less than 1% by weight of 4-chloro-2,5-difluoro-benzoyl fluoride which comprises reacting 2,4-dichloro-5-luoro-benzoyl chloride with 3.1 to 4.5 moles of potassium fluoride per mole of 2,4-dichloro-5-fluoro-benzoyl chloride in an aprotic solvent and thereafter distilling the reaction mixture.

2. The process of claim 1, in which from 1.05 to 2.0 mol of potassium fluoride are employed per equivalent of chloride atoms to be substituted.

3. The process of claim 1, in which the aprotic solvent employed is dimethyl-formamide, dimethyl sulphoxide, N-methylpyrrolidone, dimethyl sulphone or tetramethylene sulphone.

4. The process of claim 1, which is carried out at a temperature from 150° to 270° C.

5. The process of claim 1, in which the reaction time is between 1 and 12 hours.

6. The process of claim 1, which is carried out at a pressure in the range from 0.5 to 5 bar.

* * * * *

UNITED STATES PATENT AND TRADEMARK OFFICE
CERTIFICATE OF CORRECTION

PATENT NO. : 5,859,298
DATED : January 12, 1999
INVENTOR(S) : Antons, et al.

It is certified that error appears in the above-identified patent and that said Letters Patent is hereby corrected as shown below:

Col. 4, line 49    Delete " -5-luoro-benzoyl chloride " and substitute -- -5-fluoro-benzoyl chloride --

Signed and Sealed this

Twenty-sixth Day of October, 1999

Attest:

Q. TODD DICKINSON

*Attesting Officer*    *Acting Commissioner of Patents and Trademarks*